(12) United States Patent
Eriksson et al.

(10) Patent No.: US 8,410,091 B1
(45) Date of Patent: Apr. 2, 2013

(54) PROCESS FOR PREPARATION OF SUBSTITUTED 2-AMINO-5-(5-(HETEROCYCLEMETHYL)PYRIDIN-2-YLOXY)BENZOIC ACID

(75) Inventors: Magnus Carl Arne Eriksson, Brookfield, CT (US); Dhileepkumar Krishnamurthy, Brookfield, CT (US); Xiao-Jun Wang, Danbury, CT (US); Li Zhang, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/878,466

(22) Filed: Sep. 9, 2010

Related U.S. Application Data

(60) Provisional application No. 61/241,635, filed on Sep. 11, 2009, provisional application No. 61/242,018, filed on Sep. 14, 2009.

(51) Int. Cl.
*A61K 31/5513* (2006.01)
*C07D 43/00* (2006.01)
*C07D 401/04* (2006.01)

(52) U.S. Cl. ............... 514/218; 514/231.2; 514/315; 544/360; 546/184

(58) Field of Classification Search .............. 514/218, 514/231.2, 315; 544/360; 546/184
See application file for complete search history.

(56) References Cited

U.S. PATENT DOCUMENTS

| | | |
|---|---|---|
| 2007/0219176 A1* | 9/2007 | Coulombe et al. ....... 514/210.01 |
| 2010/0190779 A1 | 7/2010 | Beaulieu et al. |
| 2010/0286131 A1 | 11/2010 | Beaulieu et al. |
| 2011/0021486 A1 | 1/2011 | Beaulieu et al. |

FOREIGN PATENT DOCUMENTS

| | | |
|---|---|---|
| WO | 2009018656 A1 | 2/2009 |
| WO | 2009018657 A1 | 2/2009 |
| WO | 2009076747 A1 | 6/2009 |

OTHER PUBLICATIONS

Chen, Yunfeng "Conformational control in the regioselective synthesis of N-2-substituted-1,2,3-triazoles" The Royal Society of Chemistry, Chem. Commun. (2008) pp. 3254-3256.
Kalisiak, Jaroslaw, et al. "Efficient Synthesis of 2-Substituted-1,2,3,-triazoles" Organic Letters (2008) vol. 10, No. 15, pp. 3171-3174.
Wang, Xiao-Jun et al. "General Solution to the Synthesis of N-2 Substituted 1,2,3-Triazoles" Organic Letters (2010) vol. 12, No. 20, pp. 4632-4635.
Wang, Xiao-Jun, et al. "Bromo-Directed N-2 Alkylation of NH-1,2,3-Triazoles: Efficient Synthesis of Poly-Substituted 1,2,3-Triazoles" Organic Letters, (2009) vol. 11, No. 23, pp. 5490-5493.
Wang, Xiao-Jun, et al. "Highly Regioselective N-2 Arylation of 4,5-Dibromo-1,2,3,-triazole: Efficient Synthesis of 2-Aryltriazoles" Organic Letters, (2009) vol. 11, No. 21, 5026-5028.

* cited by examiner

*Primary Examiner* — Susannah Chung
(74) *Attorney, Agent, or Firm* — Michael P. Morris; David A. Dow

(57) ABSTRACT

The present invention is related to a process of preparing substituted 2-amino-5-(5-(heterocyclemethyl)pyridin-2-yloxy)benzoic acid compound of formula (I) or a salt thereof,

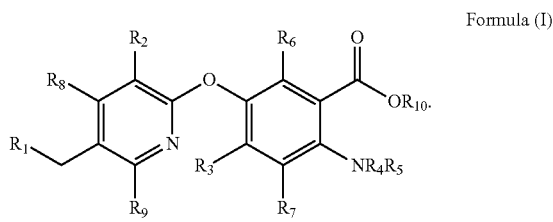

Formula (I)

13 Claims, No Drawings

PROCESS FOR PREPARATION OF SUBSTITUTED 2-AMINO-5-(5-(HETEROCYCLEMETHYL)PYRIDIN-2-YLOXY)BENZOIC ACID

This application claims benefit of U.S. Provisional Application 61/241,635 which was filed on Sep. 11, 2009 and 61,242,018 which was filed on Sep. 14, 2009, which applications are herein incorporated by reference in their entirety.

BACKGROUND OF THE INVENTION

The present invention is related to a process of preparation of a compound of substituted 2-amino-5-(5-(heterocyclemethyl)pyridin-2-yloxy)benzoic acid or a salt thereof.

Substituted 2-amino-5-(5-(heterocyclemethyl)pyridin-2-yloxy)benzoic acid has been an important intermediate in the synthesis of many biologically active compounds, including inhibitors of the hepatitis C Virus polymerase (WO 2009/076747 and WO2009/018567). The known process of preparation of the same compound in the art, while suitable for the synthesis of small quantities, is not suitable for large scale manufacture.

There is a continuing need to develop alternative processes of preparation of substituted 2-amino-5-(5-(heterocyclemethyl)pyridin-2-yloxy)benzoic acid with fewer synthetic steps, improved scalability, more efficient isolation and purification of the product, easier handling, better yields, less reaction time, less consumption of starting materials, enhanced safety, reduced contamination to the environment, and reduced costs associated with the process.

SUMMARY OF THE INVENTION

The present invention is related to a process of preparation of a compound of substituted 2-amino-5-(5-(heterocyclemethyl)pyridin-2-yloxy)benzoic acid. The present process differs from processes disclosed in the prior art, and has both technical and economical advantages over those processes, such as, for example, less expensive, commercially available starting materials, shortened synthetic steps, better yields, improved scalability, easier handling, enhanced safety, reduced contamination to the environment, and more efficient isolation and purification of the product.

DETAILED DESCRIPTION OF THE INVENTION

Definitions and Abbreviations

As used herein, the term "aryl" refers to all-carbon monocyclic, bicyclic, or polycyclic groups of 6 to 12 carbon atoms having a completely conjugated pi-electron system, which may be optionally substituted. Examples of aryl include, but are not limited to: phenyl, 4-chlorophenyl, 4-fluorophenyl, 4-bromophenyl, 3-nitrophenyl, 2-methoxyphenyl, 2-methylphenyl, 3-methylphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl, and 2-iodo-4-methylphenyl.

The term "$(C_1-C_6)$alkyl" includes both branched and straight chain alkyl groups. Typical alkyl groups contemplated by the present invention include methyl, ethyl, n-propyl, isopropyl, n-butyl, sec-butyl, isobutyl, tert-butyl, n-pentyl, isopentyl, n-hexyl, and the like.

Unless otherwise specified, the term "$(C_3-C_{12})$cycloalkyl" refers to a 3~12 carbon mono-cyclic, bicyclic, or polycyclic aliphatic ring structure, optionally substituted with for example, alkyl, alkoxy, hydroxy, oxo, and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl, and the like.

The term "halo" refers to fluoro, chloro, bromo, or iodo.

The term "salt" refers to salts prepared from chemically or pharmaceutical acceptable non-toxic acids. When a compound of the present invention is basic, its corresponding salt can be conveniently prepared from chemically or pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

TABLE 1

Abbreviations

| | |
|---|---|
| Bn | Benzyl group |
| Boc | tert-butoxycarbonyl |
| br | Broad |
| $CD_3OD$ | Deuterated methanol |
| $CDCl_3$ | Deuterated chloroform |
| d | Doublet |
| DCM | dichloromethane |
| dd | Doublet of doublets |
| DIEA | diisopropylethylamine |
| DMF | N,N-dimethylformamide |
| DMSO | dimethyl sulphoxide |
| ESI | Electrospray Ionization for mass spectrometry |
| $Et_3N$ | triethylamine |
| EtOAc | ethyl acetate |
| EtOH | ethanol |
| HCl | Hydrochloric acid |
| HRMS | High Resolution Mass Spectroscopy (electrospray ionization positive scan) |
| LCMS | Liquid Chromatography - Mass Spectroscopy |
| LRMS | Low Resolution Mass Spectroscopy (electrospray or thermospray ionization positive scan) |
| LRMS (ES⁻) | Low Resolution Mass Spectroscopy (electrospray ionization negative scan) |
| m | Multiplet |
| m/z | Mass spectrum peak |
| MeOH | methanol |
| MHz | Megahertz |
| MS | Mass spectroscopy |
| NaH | Sodium hydride |
| NMM | N-methylmorpholine |
| NMP | 1-methyl-2-pyrrolidinone |
| NMR | Nuclear Magnetic Resonance |
| Pg. | Page |
| q | Quartet |
| Rpm | Revolutions per minute |
| s | Singlet |
| t | Triplet |
| TFA | trifluoroacetic acid |
| THF | Tetrahydrofuran |
| TLC | Thin layer chromatography |
| Vol. | Volume |
| δ | Chemical shift |

One embodiment of the present invention is related to a process of preparing a compound of formula (I) or a salt thereof, Formula (I)

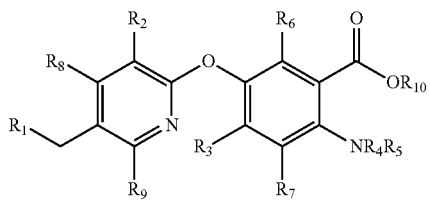

wherein $R_1$ is a heterocycle selected from the group consisting of:

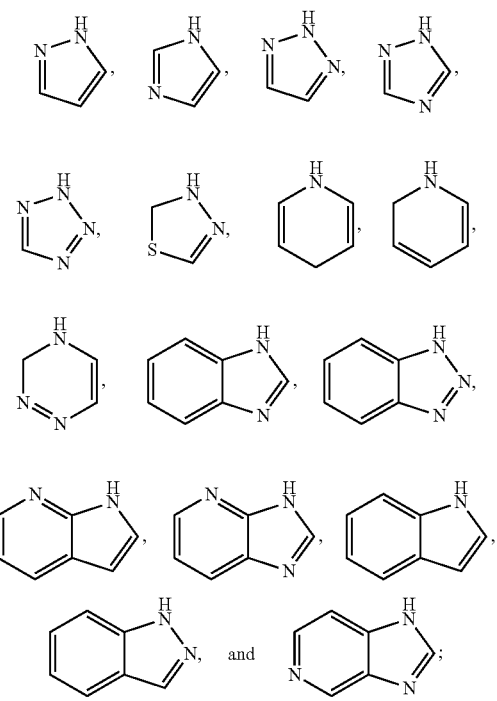

and;

$R_2$ is selected from H, F, Cl, CN, $CF_3$, $(C_{1-6})$alkyl, $(C_{3-12})$cycloalkyl and —O—$(C_{1-6})$alkyl;

$R_3$ is selected from H, F, Cl, CN, $(C_{1-6})$alkyl, —OH, —O—$(C_{1-6})$alkyl, S—$(C_{1-6})$alkyl, —$NH_2$, —NH$(C_{1-6})$alkyl, —NH$(C_{3-12})$cycloalkyl, —N$((C_{1-6})$alkyl $(C_{3-12})$cycloalkyl) and —N$((C_{1-6})$alkyl$)_2$;

$R_4$ and $R_5$ are each independently selected from H, $(C_{1-6})$alkyl, $(C_{3-12})$cycloalkyl and oxo(C(=O));

$R_6$, $R_7$, and $R_8$ are each independently selected from H, F, Cl, $(C_{1-6})$alkyl, and $(C_{3-12})$cycloalkyl;

$R_9$ is selected from H, F, Cl, $(C_{1-6})$alkyl, and $(C_{3-12})$cycloalkyl;

$R_{10}$ is selected from H, $(C_{1-6})$alkyl, and $(C_{3-12})$cycloalkyl;

wherein each of $R_1$ to $R_{10}$ is optionally substituted by one or more substituents selected from H, F, Cl, $CF_3$, OXO, $(C_{1-6})$alkyl, $(C_{3-12})$cycloalkyl, $(C_{1-6})$alkyl$(C_{3-12})$cycloalkyl, —OH, —SH, —O$(C_{1-6})$alkyl, —S$(C_{1-6})$alkyl, —$NH_2$, —NH$(C_{1-6})$alkyl and aryl; said process comprising:

Step A: converting a compound of formula (II) to a compound of formula (III) according to reaction scheme 1:

Scheme 1

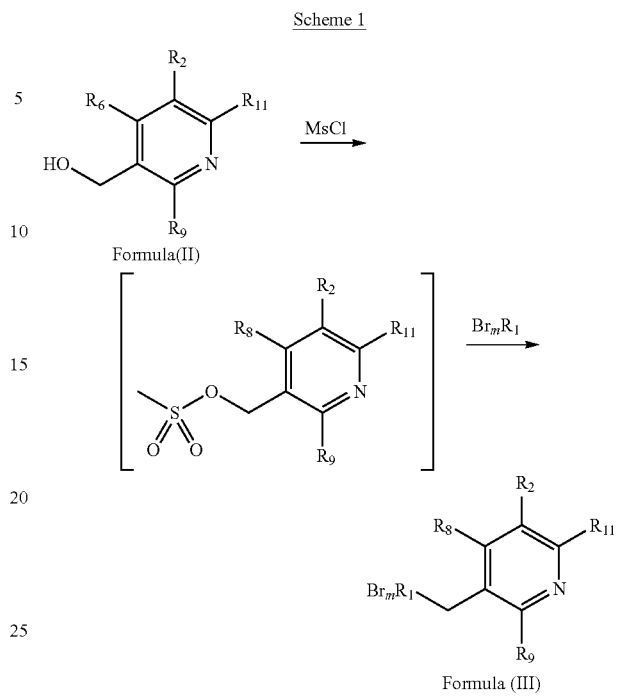

wherein the compound of Formula (II) is first reacted with methylsulfonyl chloride in the presence of a suitable solvent and at a suitable reaction temperature; upon quenching of the reaction and partially or complete removal of the solvent, the resulting mesylate intermediate is reacted with an optionally-brominated $R_1$ in the presence of a suitable base, a suitable solvent and at a suitable reaction temperature to provide the compound of formula (III) wherein m is an integer from 0 to 3 and $R_{11}$ is a halo;

Step B: converting the compound of formula (III) to a compound of formula (V) according to reaction scheme 2:

Scheme 2

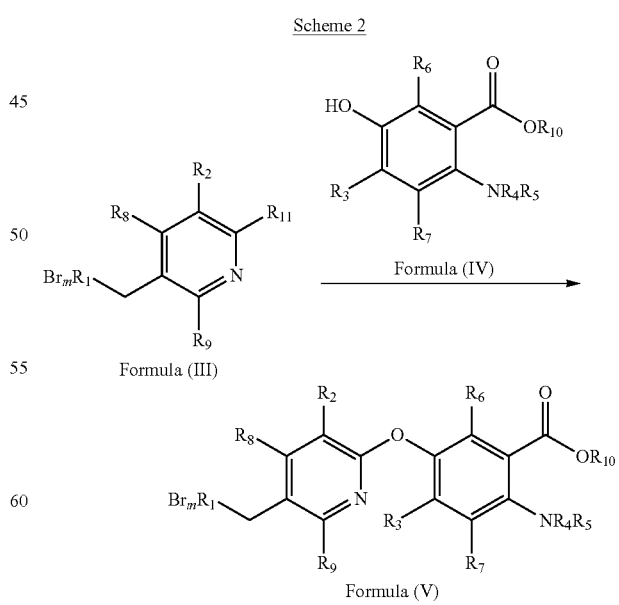

wherein the compound of formula (III) is reacted with a compound of formula (IV) or a salt thereof in the presence of a suitable base, a suitable solvent and at a suitable reaction temperature to provide the compound of formula (V); and Step C: converting the compound for formula (V) to a compound of formula (I) according to reaction scheme 3:

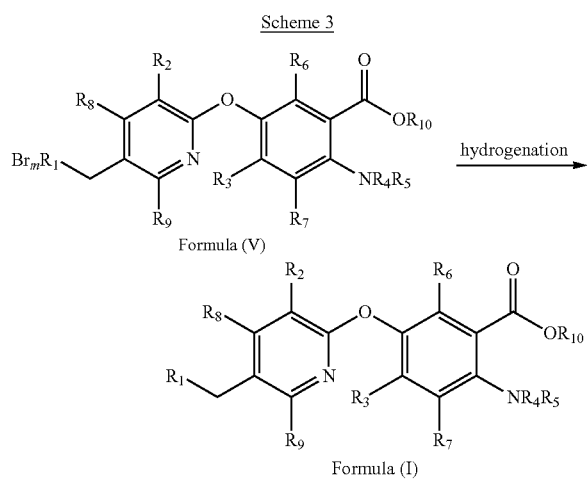

Formula (V)

Formula (I)

wherein the compound of formula (V) is hydrogenated in the presence of a suitable catalyst, a suitable solvent and at a suitable reaction temperature to provide a compound of formula (I). Preferred compounds of formula (I) include but not limited to:

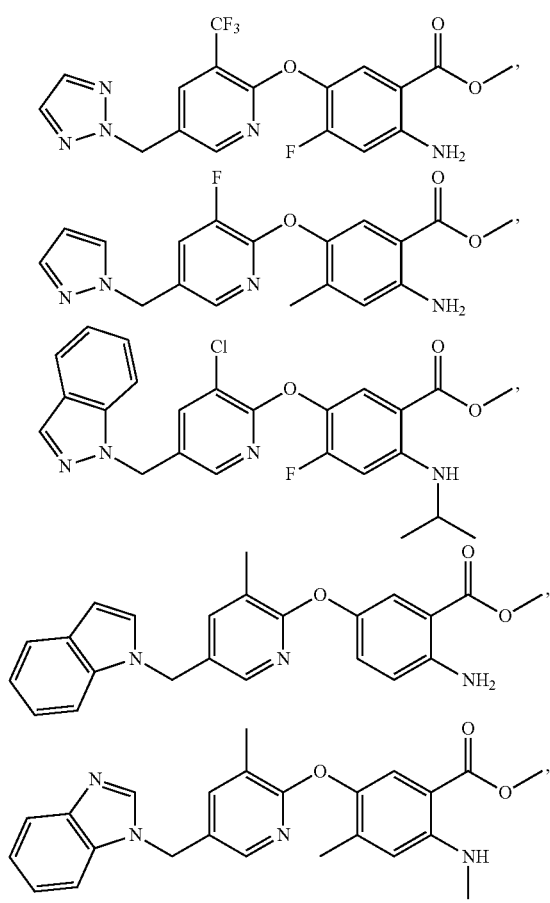

In a typical preparation of the compound of the mesylate intermediate as described in scheme 1, the compound of Formula (II) is reacted with methylsulfonyl chloride in the presence of a suitable solvent and at a suitable reaction temperature. Said suitable solvent includes, but is not limited to, N-methylmorpholine (NMM), 2-methyltetrahydrofuran (MeTHF), acetone, acetonitrile, tetrahydrofuran or mixture of two or more of the solvents. Preferably, the solvent is a mixture of NMM and MeTHF. Said reaction temperature is from 10° C. to 40° C., and preferably from 20° C. to 30° C. Upon the conversion the product is at least 99.5% pure as analyzed by HPLC, the reaction is quenched with water. Then the aqueous layer of the reaction mixture is removed, and the organic layer of the reaction mixture is washed with 10% NaCl (40 mL). The solvent in the organic layer is distilled under vacuum with internal temperature of the solvent is kept between 25° C. and 50° C., and preferably 30–45° C. During the distillation, MeTHF is added into the mixture several times to facilitate the removal of the solvent. Furthermore, a sample of the mixture is taken for Karl Fischer (KF) moisture analysis during the distillation and if the KF is over 0.2%, then an azeotropic distillation is conducted to keep the KF below 0.2%. Ultimately, the mixture is distilled to about ¼ of the original volume. The resulting mixture, where the mesylate intermediate is contained, is used for the subsequent reaction directly. The scale of the reaction is at least about 8 grams on the basis of starting material, which is the compound of formula (II). The above-described reaction is preferably carried out at about atmospheric pressure although higher or lower pressures are used if desired. Substantially, equimolar amounts of reactants are preferably used although higher or lower amounts are used if desired.

In a typical preparation of the compound of formula (III) from the above-described mesylate intermediate according to scheme 1, said mesylate intermediate is reacted with an optionally brominated heterocycle $R_1$ in the presence of a suitable base, a suitable solvent and at a suitable reaction temperature to provide the compound of formula (III). Said suitable base includes, but is not limited to, potassium carbonate, sodium carbonate, and cesium carbonate. Preferably, the base is potassium carbonate. Said suitable solvent includes, but is not limited to, dimethylformamide (DMF), N-methylmorpholine (NMM), 2-methyltetrahydrofuran (MeTHF), acetone, acetonitrile, tetrahydrofuran or mixture of two or more of the solvents. Preferably, the solvent is DMF. Said suitable reaction temperature is from −30° C. to 5° C., and preferably −20° C. to −5° C. The compound of formula (III) is purified preferably by distillation and recrystallization wherein the distillation is conducted preferably under vacuum and the internal temperature of the solvent is kept between 25° C. and 50° C., preferably 30° C. and 45° C.; and the solvent for the recrystallization includes, but is not limited to, Methyl tert-butyl ether (MTBE), hexane, ether, petroleum ether, methanol, water, ethanol, acetonitrile, tetrahydrofuran or mixture of two or more of the solvents. Preferably, the solvent for the recrystallization is a mixture of Methyl tert-butyl ether (MTBE) and hexane at a 1:1 volume ratio; and/or a mixture of methanol and water at a 20:1 volume ratio. The compound of formula (III) according to scheme 1 is obtained at a scale of at least 11 grams with at least more than 99% purity without chromatographic purification. The above-described reaction is preferably carried out at about atmospheric pressure although higher or lower pressures are used if desired. Substantially, equimolar amounts of reactants are preferably used although higher or lower amounts are used if desired.

In a typical preparation of a compound of formula (V) according to reaction scheme 2, the compound of formula (III) is reacted with a compound of formula (IV) or a salt thereof in the presence of a suitable base, a suitable solvent and at a suitable reaction temperature to provide the compound of formula (V). Preferably, the compound of formula (III) is reacted with the hydrochloride salt of the compound of formula (III). Said suitable base includes, but is not limited to, potassium carbonate, sodium carbonate, or cesium carbonate, and preferably is cesium carbonate. Said suitable solvent includes, but is not limited to, dimethylformamide (DMF), acetone, acetonitrile, tetrahydrofuran or mixture of two or more of the solvents, and preferably is DMF. Said reaction temperature is from 60° C. to 100° C., and preferably from 70° C. to 80° C. The compound of formula (V) is purified preferably by distillation wherein the distillation is preferably conducted under vacuum and the internal temperature of the solvent is kept between 25° C. and 50° C., preferably between 30° C. and 45° C. Optionally, the compound of formula (V) is further purified by running through a pad of silica gel under a suitable solvent wherein said solvent includes, but is not limited to, hexane, ethyl acetate, methanol, dichloromethane or mixture of two or more of the solvents, preferably the solvent is hexane with EtOAc at the volume ratio of 4:1. The compound of formula (V) is obtained at a scale of at least 8 grams with at least more than 97% purity. The above-described reaction is preferably carried out at about atmospheric pressure although higher or lower pressures are used if desired. Substantially, equimolar amounts of reactants are preferably used although higher or lower amounts are used if desired.

In a typical preparation of a compound of formula (I) according to reaction scheme 3, the compound of formula (V) is hydrogenated in the presence of a suitable catalyst, a suitable solvent and at a suitable reaction temperature to provide a compound of formula (I). Said catalyst includes, but is not limited to, 10% palladium on carbon. Said solvent includes, but is not limited to, methanol, ethanol, water, acetic acid or mixture of two or more of the solvents, preferably is methanol. Said reaction temperature is from 20° C. to 70° C., preferably at 30° C. The compound of formula (I) is obtained at a scale of at least 3.5 grams with at least more than 99.5% purity without purification, for example, such as chromatograph, recrystallization or distillation. In the above-described reaction, substantially, equimolar amounts of reactants are preferably used although higher or lower amounts are used if desired.

Another embodiment of the present invention is related to a process of preparation of the compound of 4,5-dibromo-2H-1,2,3-triazole according to Scheme 4:

Scheme 4

said process comprising reacting the heterocycle $R_1$ with N-Bromosuccinimide (NBS) in the presence of a suitable base, a suitable solvent and at a suitable reaction temperature to provide a brominated heterocycle $R_1$. Said base includes, but is not limited to, potassium carbonate, sodium carbonate, or cesium carbonate, and preferably is potassium carbonate. Said solvent includes, but mot limited to, isopropyl acetate (IPAc). Said reaction temperature is from 10° C. to 50° C., and preferably from 20° C. to 40° C. The compound of brominated heterocycle $R_1$ is obtained at a scale of at least 71 grams with at least more than 98% purity by the purification of distillation and/or recrystalliztion. Said distillation is preferably conducted under vacuum and the internal temperature of the solvent is kept below 50° C. Said solvent for the recrystallization includes, but is not limited to, hexane, ether, petroleum ether, methanol, water, ethanol, acetonitrile, tetrahydrofuran or a mixture of two or more of the solvents, and preferably is hexane. The above-described reaction is preferably carried out at about atmospheric pressure although higher or lower pressures are used if desired. Substantially, equimolar amounts of reactants are preferably used although higher or lower amounts are used if desired.

Another embodiment of the present invention is related to a process of preparing a compound of formula (III) or a salt thereof,

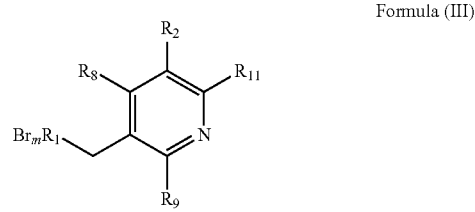

Formula (III)

wherein $R_1$ is a heterocycle selected from the group consisting of:

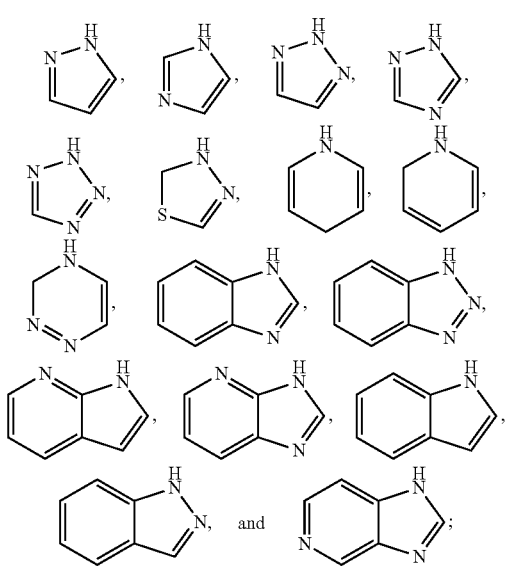

$R_2$ is selected from H, F, Cl, CN, CF$_3$, (C$_{1-6}$)alkyl, (C$_{3-12}$)cycloalkyl and —O—(C$_{1-6}$)alkyl;

$R_8$ and $R_9$ are each independently selected from H, F, Cl, (C$_{1-6}$)alkyl, and (C$_{3-12}$)cycloalkyl;

$R_{11}$ is a halo; wherein each of $R_1$, $R_2$, $R_8$ and $R_9$ is optionally substituted by one or more substituents selected from H, F, Cl, CF$_3$, OXO, (C$_{1-6}$)alkyl, (C$_{3-12}$)cycloalkyl, (C$_{1-6}$)alkyl(C$_{3-12}$)cycloalkyl, —OH, —SH, —O(C$_{1-6}$)alkyl, —S(C$_{1-6}$)alkyl, —NH$_2$, —NH(C$_{1-6}$)alkyl and aryl; and m is an integer from 0 to 3;

comprising converting a compound of formula (II) to a compound of formula (III) according to reaction scheme 5:

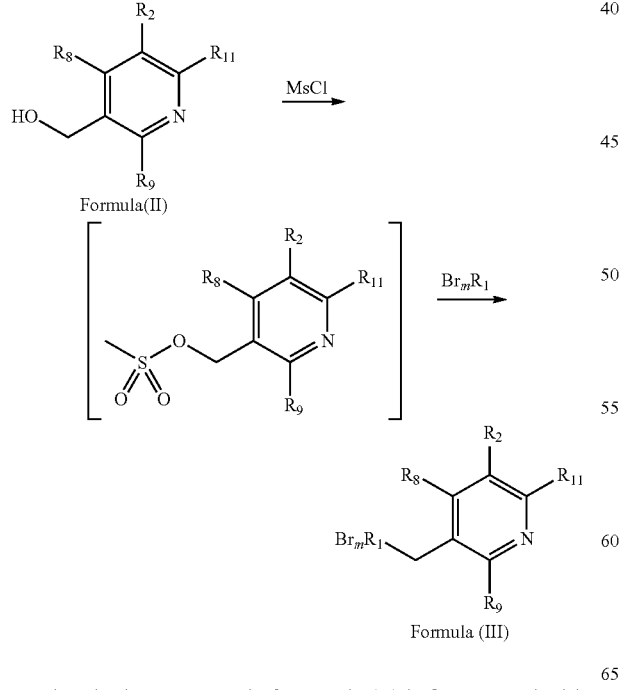

wherein the compound of Formula (II) is first reacted with methylsulfonyl chloride in the presence of a suitable solvent and at a suitable reaction temperature; upon quenching of the reaction and partially or completely removal of the solvent, the resulting mesylate intermediate is reacted with an optionally-brominated $R_1$ in the presence of a suitable base, a suitable solvent and at a suitable reaction temperature to provide the compound of formula (III). Preferred compounds of formula (III) include but not limited to:

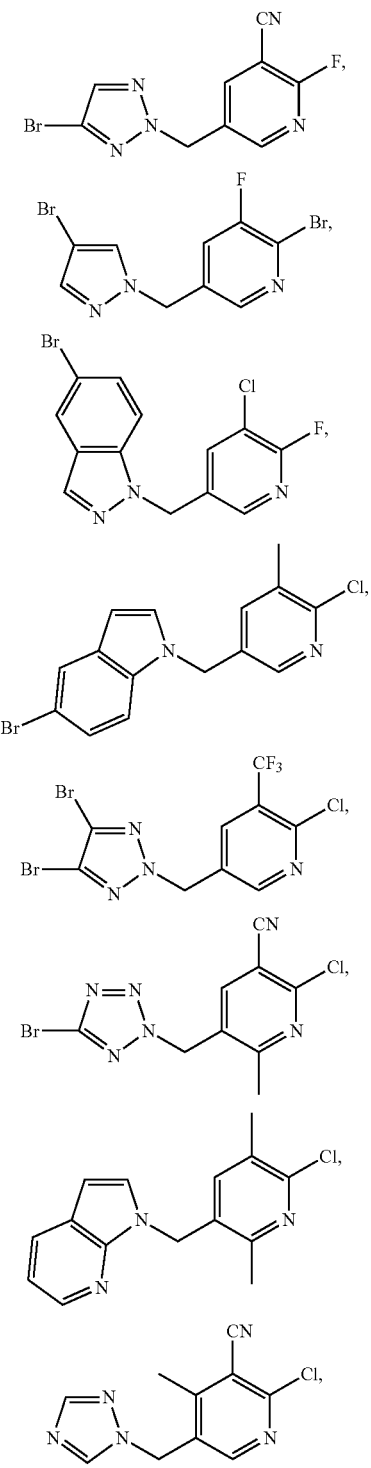

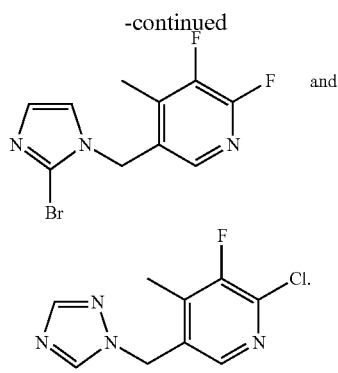

and

In a typical preparation of the compound of the mesylate intermediate as described in scheme 5, the compound of Formula (II) is reacted with methylsulfonyl chloride in the presence of a suitable solvent and at a suitable reaction temperature. Said suitable solvent includes, but is not limited to, N-methylmorpholine (NMM), 2-methyltetrahydrofuran (MeTHF), acetone, acetonitrile, tetrahydrofuran or mixture of two or more of the solvents. Preferably, the solvent is a mixture of NMM and MeTHF. Said reaction temperature is from 10° C. to 40° C., and preferably from 20° C. to 30° C. Upon the conversion the product is at least 99.5% pure as analyzed by HPLC, the reaction is quenched with water. Then the aqueous layer of the reaction mixture is removed, and the organic layer of the reaction mixture is washed with 10% NaCl. The solvent in the organic layer is distilled under vacuum with internal temperature of the solvent is kept between 25° C. and 50° C., and preferably 30~45° C. During the distillation, MeTHF is added into the mixture several times to facilitate the removal of the solvent. Furthermore, a sample of the mixture is taken for Karl Fischer (KF) moisture analysis during the distillation and if the KF is over 0.2%, then an azeotropic distillation is conducted to keep the KF below 0.2%. Ultimately, the mixture is distilled to about ¼ of the original volume. The resulting mixture, where the mesylate intermediate is contained, is used for the subsequent reaction directly. The scale of the reaction is at least about 8 grams on the basis of starting material, which is the compound of formula (II). The above-described reaction is preferably carried out at about atmospheric pressure although higher or lower pressures are used if desired. Substantially, equimolar amounts of reactants are preferably used although higher or lower amounts are used if desired.

In a typical preparation of the compound of formula (III) from the above-described mesylate intermediate according to scheme 5, said mesylate intermediate is reacted with an optionally brominated heterocycle $R_1$ in the presence of a suitable base, a suitable solvent and at a suitable reaction temperature to provide the compound of formula (III). Said suitable base includes, but is not limited to, potassium carbonate, sodium carbonate, and cesium carbonate. Preferably, the base is potassium carbonate. Said suitable solvent includes, but is not limited to, dimethylformamide (DMF), N-methylmorpholine (NMM), 2-methyltetrahydrofuran (MeTHF), acetone, acetonitrile, tetrahydrofuran or mixture of two or more of the solvents. Preferably, the solvent is DMF. Said suitable reaction temperature is from −30° C. to 5° C., and preferably −20° C. to −5° C. The compound of formula (III) is purified preferably by distillation and recrystallization wherein the distillation is conducted preferably under vacuum and the internal temperature of the solvent is kept between 25° C. and 50° C., preferably 30° C. and 45° C.; and the solvent for the recrystallization includes, but is not limited to, Methyl tert-butyl ether (MTBE), hexane, ether, petroleum ether, methanol, water, ethanol, acetonitrile, tetrahydrofuran or mixture of two or more of the solvents. Preferably, the solvent for the recrystallization is a mixture of Methyl tert-butyl ether (MTBE) and hexane at a 1:1 volume ratio; and/or a mixture of methanol and water at a 20:1 volume ratio. The compound of formula (III) according to scheme 5 is obtained at a scale of at least 11 grams with at least more than 99% purity without chromatograph purification. The above-described reaction is preferably carried out at about atmospheric pressure although higher or lower pressures are used if desired. Substantially, equimolar amounts of reactants are preferably used although higher or lower amounts are used if desired.

All processes of preparation, as described above, are supplemented by synthetic methods known in the art of organic chemistry, or modifications and derivatisations that are familiar to those of ordinary skill in the art. The starting materials used herein are commercially available or may be prepared by routine methods known in the art (such as those methods disclosed in standard reference books such as the COMPENDIUM OF ORGANIC SYNTHETIC METHODS, Vol. I-VI (published by Wiley-Interscience)).

During any of the above and/or following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference.

EXAMPLES

The features and advantages of the invention are more fully shown by the following non-limiting examples. These examples illustrate the process of preparation of various compounds of the present invention. Additional compounds within the scope of this invention can be prepared using the methods illustrated in these Examples, either alone or in combination with techniques generally known in the art. As is well known to a person skilled in the art, reactions are performed in an inert atmosphere (including but not limited to nitrogen or argon) where necessary to protect reaction components from air or moisture. Temperatures are given in degrees Celsius (° C.). Solution percentages and ratios express a volume to volume relationship, unless stated otherwise. Flash chromatography is carried out on silica gel ($SiO_2$) according to the procedure of W. C. Still et al., J. Org. Chem., (1978), 43, 2923.

Reactions were monitored by thin layer chromatography (TLC) and/or HPLC. For the TLC, it was conducted on silica gel 60 $F_{254}$ (0.2 mm) precoated aluminum foil and visualized using UV light. Analytical HPLC is carried out under standard conditions using a Agilent™ Eclipse XDB-C8 reverse phase column, 150×4.6 mm (or 50×4.6 mm) i.d., 5 (or 3.5) μM, elution with a mobile phases of 0.05% trifluoroacetic acid in HPLC grade water (A) and 0.05% trifluoroacetic acid in HPLC grade acetonitrile (B). The flow rate and run time are adjusted to the samples being analyzed. Non-limiting examples of flow rate are 1.0 or 2.0 mL/min, and non-limiting examples of run time are 5 or 14 min., and post-run time is 1.0 or 3.0 min. The gradient profile is adjusted to the samples being analyzed, for example, 0.00 min 95% A, 4.00 min 70% A, 10.00 min 10% A, 11.00 min 5% A and 14.00 min 5% A; or 0.00 min 95% A, 3.5 min 5% A, 4.5 min 5% A, 4.7 min 90% A and 5.0 min 95% A for analytical. UV detection is at 230 and/or 254 nm. $^1$HNMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +(CH or CH$_3$), –(CH$_2$), $C_{quart}$(C).

Example 1

Preparation of 5-((5-bromo-2H-tetrazol-2-yl)methyl)-2-chloronicotinonitrile

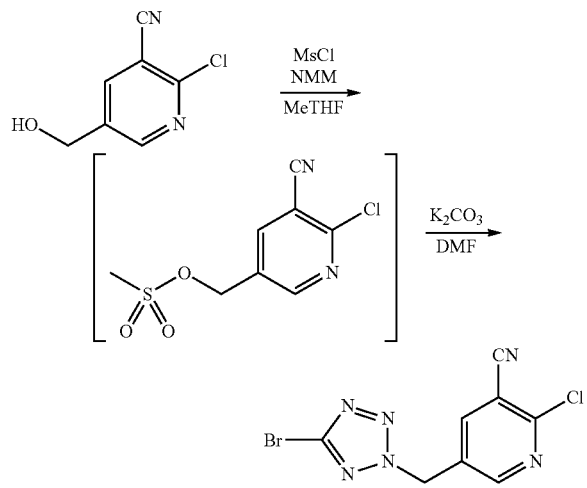

N-methylmorpholine (NMM, 7.9 mL, 72.0 mmol) and 2-methyltetrahydrofuran (MeTHF, 60 mL) are added to a 250 mL 3-neck round bottom flask. Then, methylsulfonyl chloride (MsCl, 5.6 mL, 72.0 mmol) is slowly added into the flask by keeping internal temperature of the reaction mixture between 20~30° C. The reaction mixture is then stirred for 10 min at 20° C. Subsequently, 2-chloro-5-(hydroxymethyl)nicotinonitrile (6.1 g, 36.0 mmol) in MeTHF (40 mL) is slowly added into the flask over 10 min by keeping internal temperature of the reaction mixture between 20~40° C. The reaction mixture is then stirred at 25° C. for 1 h. A sample of the reaction mixture is taken for HPLC analysis. The reaction mixture is kept stifling until the conversion to product was at least 99.5%. Then, the reaction is quenched with water (40 mL), and the reaction mixture is stirred for 10 min. Then the aqueous layer of the reaction mixture is removed, and the organic layer of the reaction mixture is washed with 10% NaCl (40 mL). The solvent in the organic layer is distilled under vacuum with internal temperature between 30~45° C. to ⅙ of original volume. Then MeTHF (50 mL) is added into the solvent, and the resulting solvent is distilled under vacuum with internal temperature between 30~45° C. to ¼ of original volume. Another 50 ml of MeTHF is added into the solvent, and a sample of the resulting solvent is taken for KF analysis. If the KF is over 0.2%, then an azeotropic distillation is conducted to keep the KF below 0.2%. Then, the solvent is distilled under vacuum with internal temperature between 30~45° C. to ¼ of original volume. The resulting solvent into which the mesylate intermediate is dissolved is used for the subsequent reaction directly.

5-bromo-2H-tetrazole (5.2 g, 35.3 mmol) and then DMF (100 mL) are added into the above-described solvent where the mesylate intermediate is dissolved into. The reaction mixture is then cooled to –20° C., and K$_2$CO$_3$ (12.19 g, 88.2 mmol) is added into. The reaction is then warmed to –5° C. and is stirred for 16 h. A sample of the reaction mixture is taken for HPLC analysis. The reaction mixture is continually stirred until the conversion to product was at least 99%. Then, the reaction is quenched with water (100 mL) and MTBE (100 mL). The bottom aqueous layer is then removed. The organic layer is washed with 5% NaCl (100 mL). The solvent of the organic layer is then distilled under vacuum with internal temperature of the solvent as between 30~45° C. to ⅙ of original volume. Then MeOH (100 mL) is added into the solvent, and the resulting solvent is distilled under vacuum with internal temperature of the solvent as between 30~45° C. to ⅙ of original volume. Then, another 50 ml of MeOH is added into the solvent and the resulting solvent is distilled under vacuum with internal temperature of the solvent as between 30~45° C. to ⅕ of original volume. Subsequently, MeOH (50 mL) and water (2.5 mL) are added into the solvent, and the mixture is heated to 55° C. and then cooled down to 20° C. in 2 h to afford a slurry. The slurry is stirred at 20° C. for 1 h and filtered. The filter cake is washed with 10:1 MeOH/water (5.5 mL) and is dried under vacuum to afford product with over 99% purity. The filter is collected and the solvent was removed. Most of the wrong isomer in the filter is removed by crystallization in 1:1 MTBE/hexanes at room temperature. The enriched crude product is then crystallized from 20:1 MeOH/water to afford additional product with over 99% purity. The total amount of the obtained product is about 8 g.

Other R$_1$ heretocycles as contemplated in the present invention can be connected to the substituted 3-methylpyridine via similar preparation procedures as outlined above.

Example 2

Preparation of 4,5-dibromo-2H-1,2,3-triazole

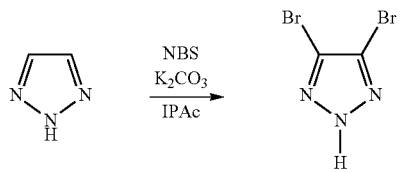

NBS (123 g, 690 mmol), K$_2$CO$_3$ (0.8 g, 5.8 mmol) and IPAc (300 mL) are added into a round bottom flask with the internal temperature of the flask keep at 20° C. Then, 1H-1,2,3-triazole (19 mL, 330 mmol) is slowly added in the flask by keeping internal temperature of the reaction mixture below 40° C. The reaction mixture is stirred at 20° C. for 5 h, and then filtered. The filter cake is washed with IPAc (30 mL), and then the filter cake is discarded. The filtrate is washed with 2% NaS$_2$O$_3$ (100 mL). The solvent of the resulting organic layer is distilled under vacuum and the internal temperature of the solvent is kept below 45° C. After the distillation, the obtained product is recrystallized by hexanes (600 mL). The resulting solid is filtered, and the filter cake is washed with hexanes (60 mL). The resulting solid is dried under vacuum at a temperature of no more than 35° C. to afford 70.8 grams of the product.

Other $R_1$ heterocycles as contemplated in the present invention can be brominated via similar preparation procedures as outlined above.

Example 3

Preparation of methyl 5-(3-cyano-5-((3,5-dibromo-1H-1,2,4-triazol-1-yl)methyl)-4-methylpyridin-2-yloxy)-2-(cyclopropylamino)-3-methylbenzoate

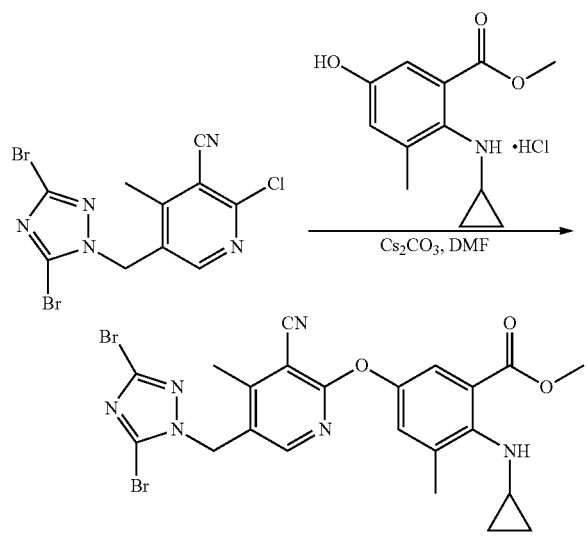

$Cs_2CO_3$ (14.9 g, 45.8 mmol) and DMF (25 mL) are added into a 250 mL flask, and the reaction mixture is heated to 80° C. 2-chloro-5-((3,5-dibromo-1H-1,2,4-triazol-1-yl)methyl)-4-methylnicotinonitrile (7.2 g, 18.3 mmol) and hydrochloride salt of methyl 2-(cyclopropylamino)-5-hydroxy-3-methylbenzoate (4.2 g, 18.3 mmol) is dissolved by DMF (25 mL) in a 100 mL flask, and the mixture is added into the 250 ml flask over 30 min. The resulting mixture is stirred at 80° C. for 30 min. A sample of the mixture is taken for HPLC analysis. The reaction mixture is kept stifling until the conversion to product is at least 99%. Then, the reaction mixture is cooled to 20° C., and the reaction is quenched with EtOAc (50 mL) and water (50 mL). The bottom aqueous layer is then removed, and the organic layer is washed with two times of 10% NaCl (40 mL each). The solvent of the organic layer is distilled under vacuum with internal temperature of the solvent as between 30~45° C. to ⅙ of original volume. Then the resulting solvent is passed through a pad of silica gel (15 g) by 4:1 hexanes/EtOAc (100 mL). The resulting solvent is then distilled under vacuum with internal temperature of the solvent as between 30~45° C. to ⅛ of original volume. Then MeOH (70 mL) is added into the solvent, and the resulting solvent is distilled under vacuum with internal temperature of the solvent as between 30~45° C. to ⅛ of original volume. Another 70 ml of MeOH is added into the solvent, and the resulting solvent is distilled under vacuum with internal temperature of the solvent as between 30~45° C. to ⅛ of original volume. An additional 70 ml of MeOH is added into the solvent, and the resulting solvent is heated to 60° C., then is cooled down to 20° C. in 2 h and stirred at 20° C. for 2 h. The resulting mixture is filtered, and the filter cake is washed with MeOH (15 mL). The filter cake is then dried under vacuum at 20° C. to afford 8 g product with more than 97% purity.

Other compounds of the three-ring structure (heterocycle-pyridine-phenyl) as contemplated in the present invention can be prepared via similar preparation procedures as outlined above.

Example 4

Preparation of methyl 5-(5-((2H-1,2,3-triazol-2-yl)methyl)-3-(trifluoromethyl)pyridin-2-yloxy)-2-amino-4-fluorobenzoate (Formula (I))

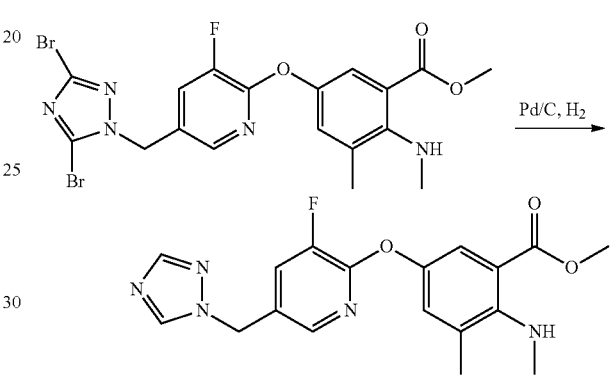

3.7 g (7.03 mmol) of methyl 5-(5-((3,5-dibromo-1H-1,2,4-triazol-1-yl)methyl)-3-fluoropyridin-2-yloxy)-3-methyl-2-(methylamino)benzoate is added into in an autoclave, followed by the addition of 0.8 g of 10% Pd/C 50% wet (0.38 mmol, 5.3 mol %) and 40 mL methanol. The autoclave is purged with $N_2$ three times by pressurizing to 100 psi then venting to 5 psi. The autoclave was then heated to 30° C., and then is pressurized with hydrogen to 300 psi. The reaction mixture is stirred under 400~800 rpm for 9 h, and sample of the reaction mixture is taken for HPLC analysis until complete conversion is determined. After the reaction is finished, the reaction mixture is filtered through Celite, and the filter cake is washed with 10 mL MeOH. The filter is evaporated and dried under vacuum to afford 2.6 g product with more than 99.5% purity.

Other compounds as contemplated in the present invention can be prepared via the similar preparation procedures as outlined above.

The invention claimed is:

1. A process of preparing a compound of formula (I) or a salt thereof,

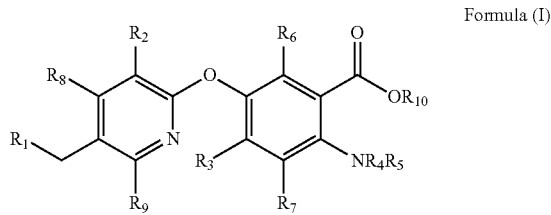

Formula (I)

wherein $R_1$ is a heterocycle selected from the group consisting of:

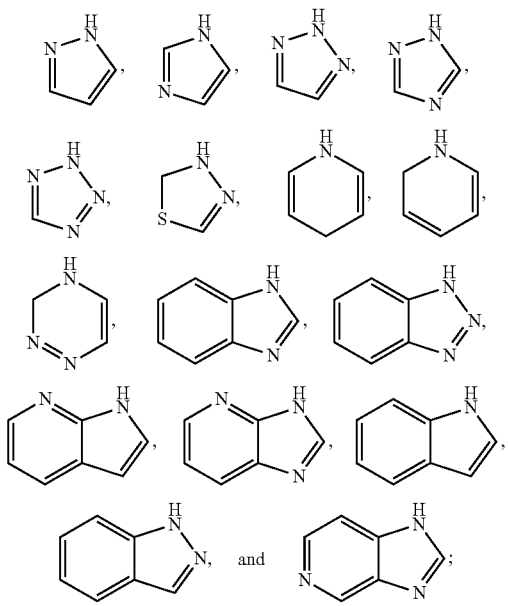

$R_2$ is selected from H, F, Cl, CN, $CF_3$, $(C_{1-6})$alkyl, $(C_{3-12})$cycloalkyl and —O—$(C_{1-6})$alkyl;

$R_3$ is selected from H, F, Cl, CN, $(C_{1-6})$alkyl, —OH, —O—$(C_{1-6})$alkyl, S—$(C_{1-6})$alkyl, —$NH_2$, —NH$(C_{1-6})$alkyl, —NH$(C_{3-12})$cycloalkyl, —N($(C_{1-6})$alkyl $(C_{3-12})$cycloalkyl) and —N($(C_{1-6})$alkyl$)_2$;

$R_4$ and $R_5$ are each independently selected from H, $(C_{1-6})$alkyl, $(C_{3-12})$cycloalkyl and oxo (C(=O));

$R_6$, $R_7$, and $R_8$ are each independently selected from H, F, Cl, $(C_{1-6})$alkyl, and $(C_{3-12})$cycloalkyl;

$R_9$ is selected from H, F, Cl, $(C_{1-6})$alkyl, and $(C_{3-12})$cycloalkyl;

$R_{10}$ is selected from H, $(C_{1-6})$alkyl, and $(C_{3-12})$cycloalkyl;

wherein each of $R_1$ to $R_{10}$ is optionally substituted by one or more substituents selected from H, F, Cl, $CF_3$, OXO, $(C_{1-6})$alkyl, $(C_{3-12})$cycloalkyl, $(C_{1-6})$alkyl$(C_{3-12})$cycloalkyl, —OH, —SH, —O$(C_{1-6})$alkyl, —S$(C_{1-6})$alkyl, —$NH_2$, —NH$(C_{1-6})$alkyl and aryl;

comprising:

Step A: converting a compound of formula (II) to a compound of formula (III) according to reaction scheme 1:

Scheme 1

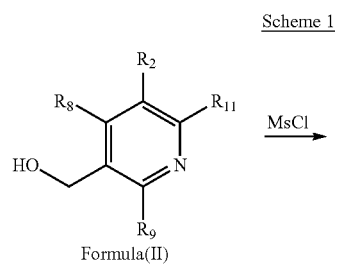

Formula(II)

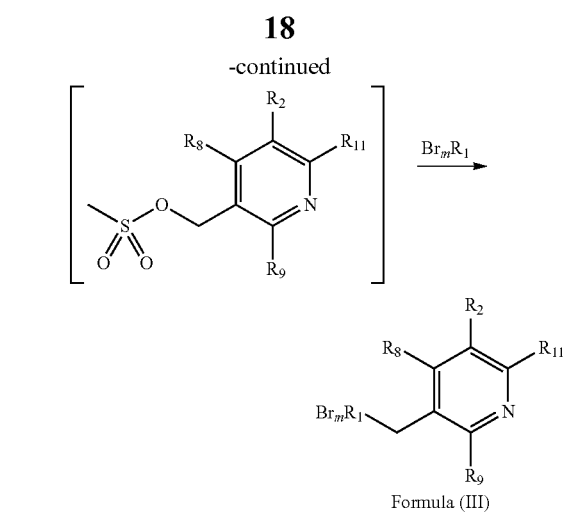

Formula (III)

wherein the compound of Formula (II) is first reacted with methylsulfonyl chloride in the presence of a suitable solvent and at a suitable reaction temperature; upon quenching of the reaction and partially or completely removal of the solvent, the resulting mesylate intermediate is reacted with an optionally-brominated $R_1$ in the presence of a suitable base, a suitable solvent and at a suitable reaction temperature to provide the compound of formula (III) wherein m is an integer from 0 to 3 and $R_{11}$ is a halo;

Step B: converting the compound of formula (III) to a compound of formula (V) according to reaction scheme 2:

Scheme 2

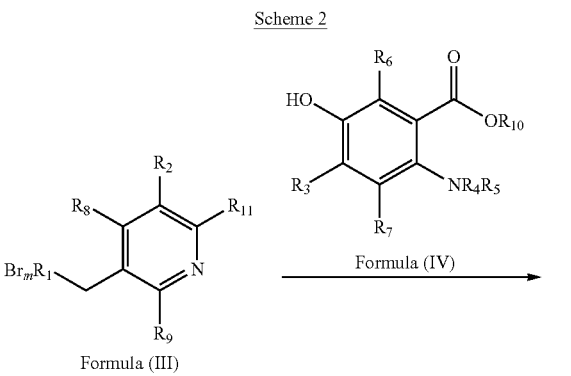

Formula (III)          Formula (IV)

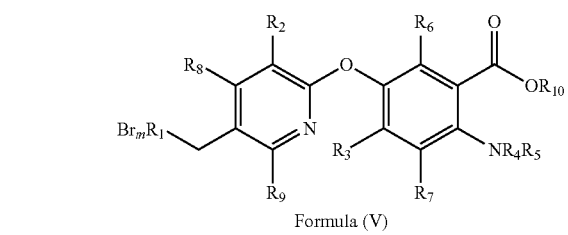

Formula (V)

wherein the compound of formula (III) is reacted with a compound of formula (IV) or a salt thereof in the presence of a suitable base, a suitable solvent and at a suitable reaction temperature to provide the compound of formula (V); and Step C: converting the compound for formula (V) to a compound of formula (I) according to reaction scheme 3:

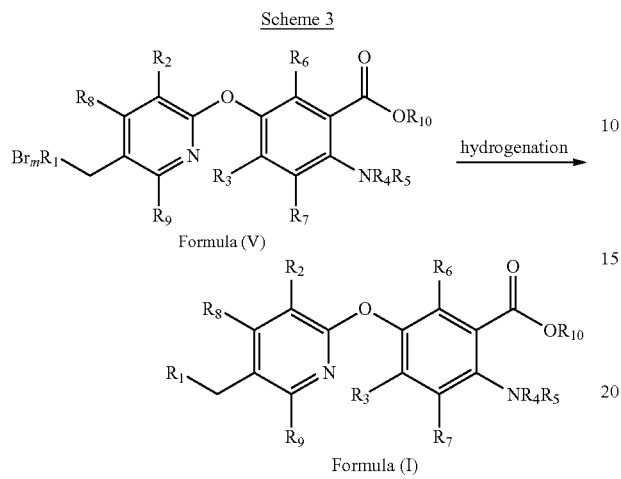

wherein the compound of formula (V) is hydrogenated in the presence of a suitable catalyst, a suitable solvent and at a suitable reaction temperature to provide a compound of formula (I).

2. The process of claim 1, wherein the brominated compound in scheme 1 of Step A is synthesized according to Scheme 4:

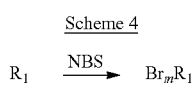

wherein $R_1$ is reacted with N-Bromosuccinimide (NBS) in the presence of a suitable base, a suitable solvent and at a suitable reaction temperature to provide the brominated $R_1$.

3. The process of claim 2, wherein the compound of brominated $R_1$ is obtained at a scale of at least 71 grams with at least more than 98% purity.

4. The process of claim 1, wherein the synthesis of said resulting mesylate intermediate of Step A, said solvent comprises N-methylmorpholine (NMM), 2-methyltetrahydrofuran (MeTHF), acetone, acetonitrile, tetrahydrofuran or a mixture of two or more of the solvents.

5. The process of claim 1, wherein the synthesis of the compound of formula (III) from the resulting mesylate intermediate of Step A, said solvent comprises dimethylformamide (DMF), N-methylmorpholine (NMM), 2-methyltetrahydrofuran (MeTHF), acetone, acetonitrile, tetrahydrofuran or mixture of two or more of the solvents.

6. The process of claim 1, wherein the synthesis of the compound of formula (III) from the resulting mesylate intermediate of Step A, the compound of formula (III) is purified by distillation and/or recrystallization.

7. The process of claim 1, wherein the compound of formula (III) of Step A is obtained at a scale of at least 11 grams with at least more than 99% purity.

8. The process of claim 1, wherein the compound of formula (III) is reacted with the hydrochloride salt of the compound of formula (IV) of Step B.

9. The process of claim 1, wherein said base of Step B comprises potassium carbonate, sodium carbonate, or cesium carbonate.

10. The process of claim 1, wherein said solvent of Step B comprises dimethylformamide (DMF), acetone, acetonitrile, tetrahydrofuran or mixture of two or more of the solvents.

11. The process of claim 1, where the compound of formula (I) is selected from the group consisting of:

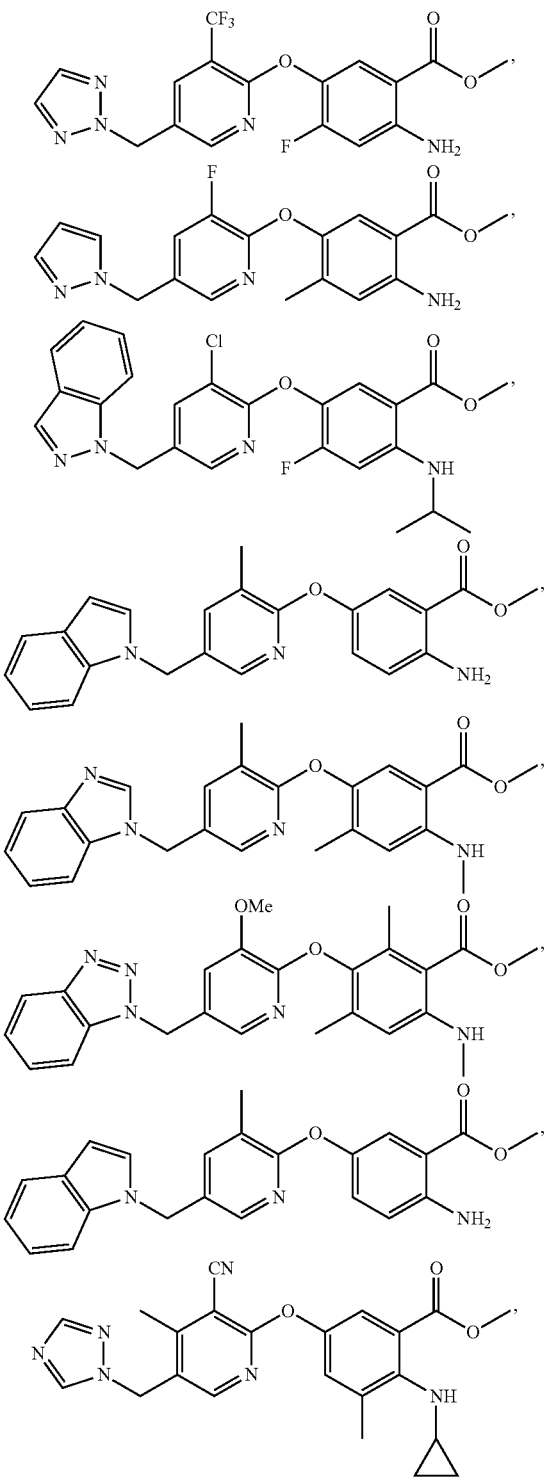

-continued

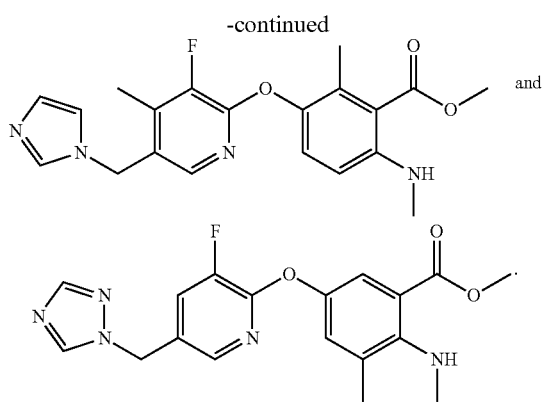

and

12. A process of preparing a compound of formula (III) or a salt thereof,

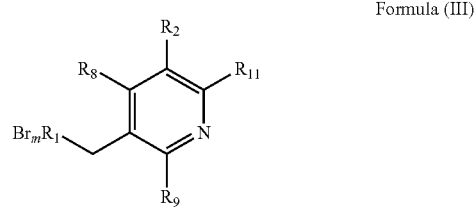

Formula (III)

wherein
R₁ is a heterocycle selected from the group consisting of:

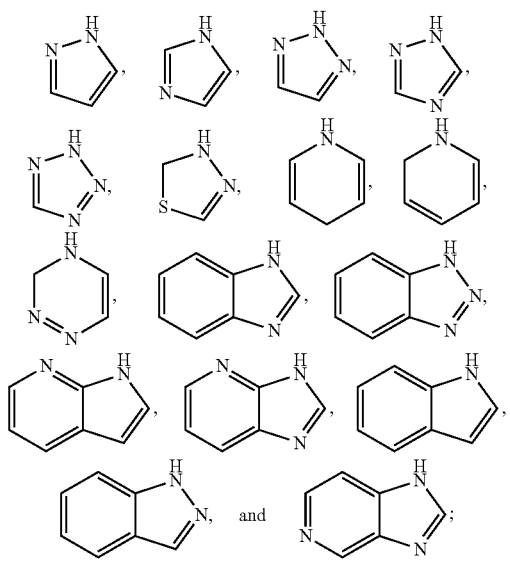

$R_2$ is selected from H, F, Cl, CN, CF$_3$, (C$_{1-6}$)alkyl, (C$_{3-12}$) cycloalkyl and —O—(C$_{1-6}$)alkyl;
$R_8$ and $R_9$ are each independently selected from H, F, Cl, (C$_{1-6}$)alkyl, and (C$_{3-12}$)cycloalkyl;
$R_{11}$ is a halo; wherein each of $R_1$, $R_2$, $R_8$ and $R_9$ is optionally substituted by one or more substituents selected from H, F, Cl, CF$_3$, OXO, (C$_{1-6}$)alkyl, (C$_{3-12}$)cycloalkyl, (C$_{1-6}$)alkyl(C$_{3-12}$)cycloalkyl, —OH, —SH, —O(C$_{1-6}$) alkyl, —S(C$_{1-6}$)alkyl, —NH$_2$, —NH(C$_{1-6}$)alkyl and aryl; and
m is an integer from 0 to 3;

comprising converting a compound of formula (II) to a compound of formula (III) according to reaction scheme 5:

Scheme 5

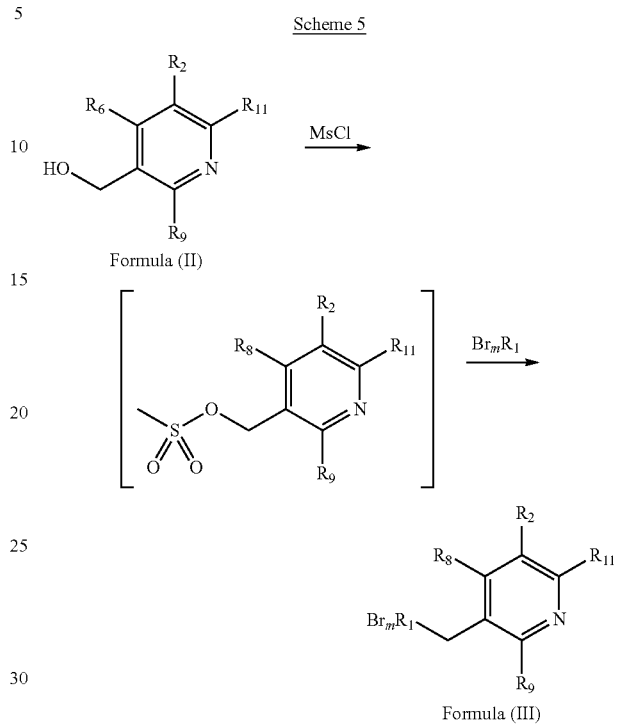

wherein the compound of Formula (II) is first reacted with methylsulfonyl chloride in the presence of a suitable solvent and at a suitable reaction temperature; upon quenching of the reaction and partially or completely removal of the solvent, the resulting mesylate intermediate is reacted with an optionally-brominated R₁ in the presence of a suitable base, a suitable solvent and at a suitable reaction temperature to provide the compound of formula (III).

13. The process of claim 12 where the compound of formula (III) is selected from the group consisting of:

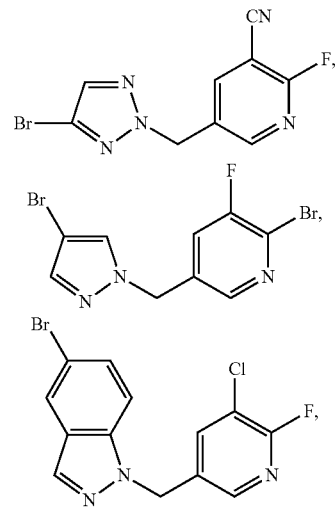

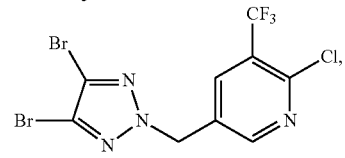
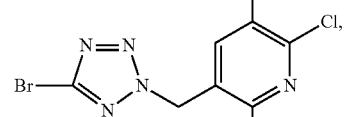
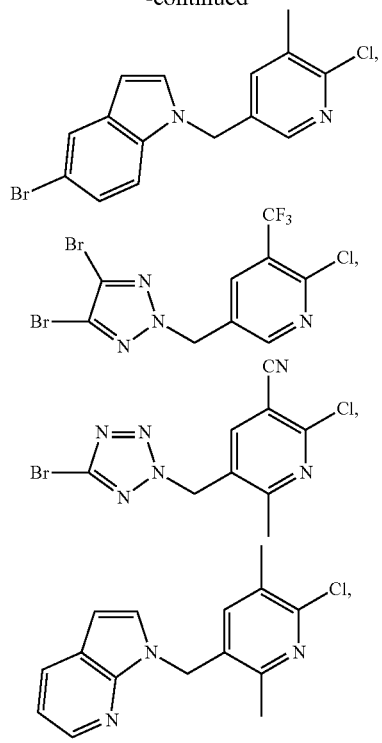
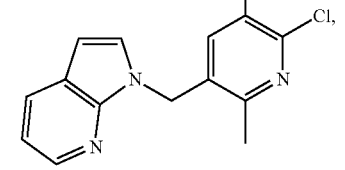
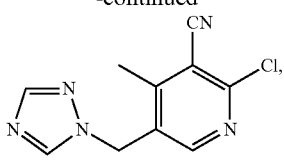
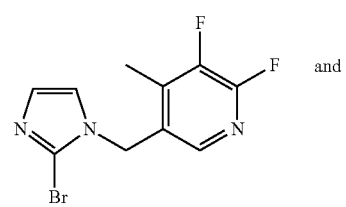
and
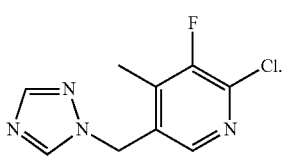
* * * * *